United States Patent
Pons et al.

(10) Patent No.: US 6,975,905 B2
(45) Date of Patent: Dec. 13, 2005

(54) STIMULATION CIRCUITS FOR A CYCLE TO CYCLE STIMULATION THRESHOLD CAPTURE FOR AN ACTIVE IMPLANTABLE CARDIAC DEVICE

(75) Inventors: Pascal Pons, Crolles (FR); Renzo Dal Molin, Chatillon (FR)

(73) Assignee: ELA Medical S.A., Montrouge (FR)

( * ) Notice: Subject to any disclaimer, the term of this patent is extended or adjusted under 35 U.S.C. 154(b) by 540 days.

(21) Appl. No.: 10/073,095

(22) Filed: Feb. 8, 2002

(65) Prior Publication Data

US 2002/0147477 A1    Oct. 10, 2002

(30) Foreign Application Priority Data

Feb. 9, 2001   (FR) .................................. 01 01797

(51) Int. Cl.[7] ............................................. A61N 1/362
(52) U.S. Cl. ............................................. 607/34; 607/9
(58) Field of Search ........................... 607/4, 9, 11–12, 607/27–28, 34

(56) References Cited

U.S. PATENT DOCUMENTS

| | | | |
|---|---|---|---|
| 4,096,866 A | * | 6/1978 | Fischell .................. 607/34 |
| 5,111,816 A | * | 5/1992 | Pless et al. .............. 607/4 |
| 5,411,533 A | | 5/1995 | Dubreuil et al. |
| 5,591,211 A | | 1/1997 | Meltzer .................. 607/5 |
| 5,735,880 A | * | 4/1998 | Prutchi et al. ........... 607/9 |
| 5,846,264 A | * | 12/1998 | Andersson et al. ....... 607/28 |
| 5,948,004 A | * | 9/1999 | Weijand et al. .......... 607/9 |
| 6,002,962 A | | 12/1999 | Huang et al. ............ 607/5 |
| 6,169,921 B1 | | 1/2001 | Knight et al. ........... 607/4 |
| 6,238,419 B1 | * | 5/2001 | Lindgren ................. 607/9 |
| 6,456,877 B1 | * | 9/2002 | Fishler .................. 607/5 |
| 6,615,089 B1 | * | 9/2003 | Russie et al. ........... 700/21 |

FOREIGN PATENT DOCUMENTS

| | | | |
|---|---|---|---|
| EP | 0 813 889 A3 | 12/1997 | .......... A61N 1/368 |
| WO | WO 93/02741 | 2/1993 | ............ A61N 1/36 |

* cited by examiner

*Primary Examiner*—Kennedy Schaetzle
*Assistant Examiner*—Kristen Mullen
(74) *Attorney, Agent, or Firm*—Orrick Herrington & Sutcliffe, LLP

(57) ABSTRACT

A circuit for delivering a back-up stimulation voltage in a cycle to cycle capture test for an active implantable medical device such as a pacemaker, defibrillator and/or cardiovertor or a multisite device having an enhanced circuit for delivering back-up stimulation pulses. This device comprises a first stimulation stage having: a output capacitor (12); a charging circuit (14) to charge the output capacitor to a first predetermined voltage (V1) for the stimulation that is close to the threshold of effectiveness for the stimulation of the patient; a first switch (18) that is able to connect the output capacitor to a stimulation terminal (16) of the device; a capture test circuit that is able to determine, after delivery of a stimulation, whether the stimulation was effective or if, on the contrary, there was loss of capture; a circuit for readjusting the stimulation voltage according to the result of the capture test; and a circuit able to deliver a backup-stimulation after the capture test if the result of the capture test reveals a loss of capture. The circuit for delivering a backup-stimulation includes an additional capacitor that is maintained charged, and a second switch (34), able to connect the additional capacitor to the aforementioned stimulation terminal (16) of the device to deliver the back-up stimulation pulse.

12 Claims, 2 Drawing Sheets

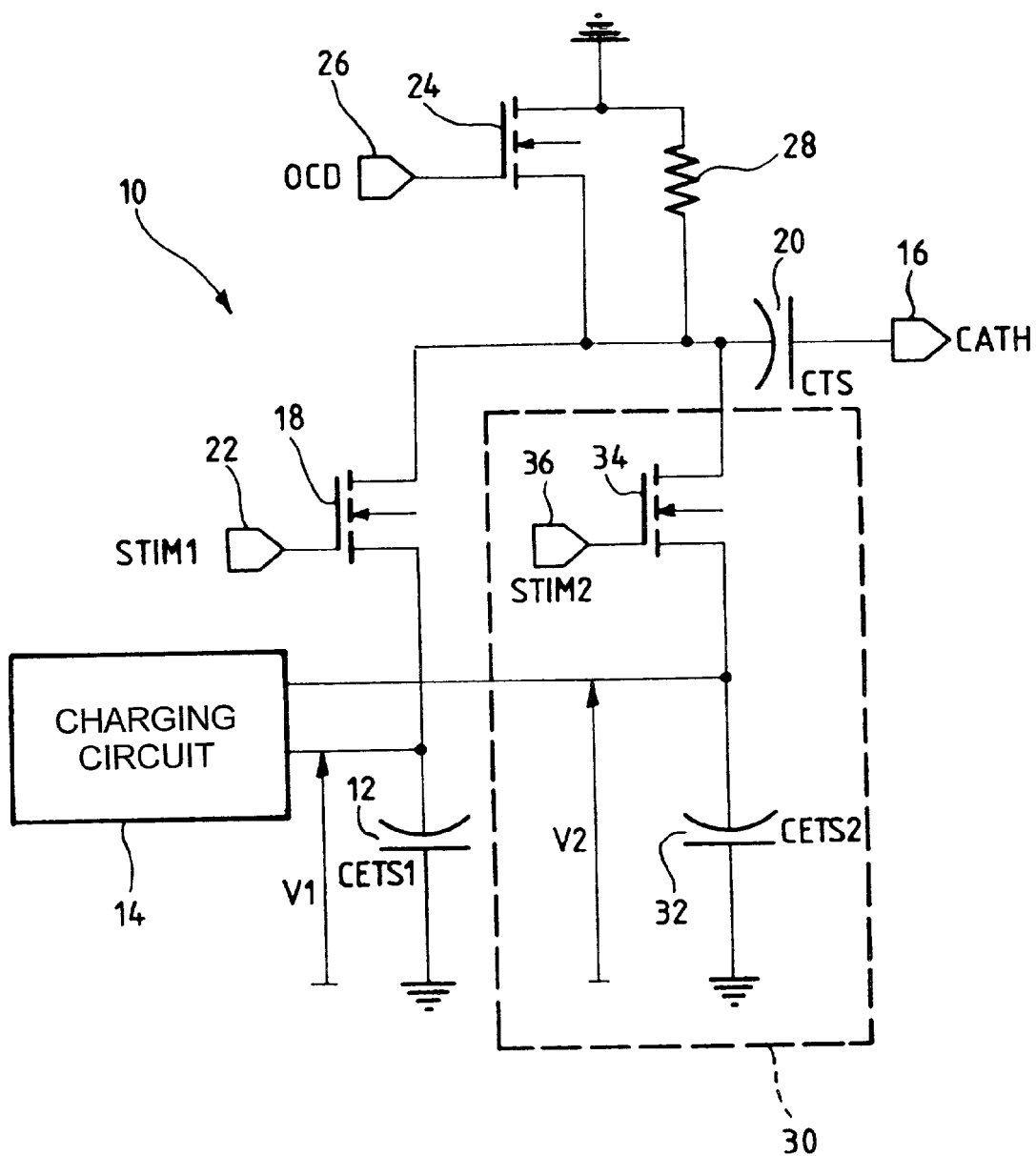
FIG_1

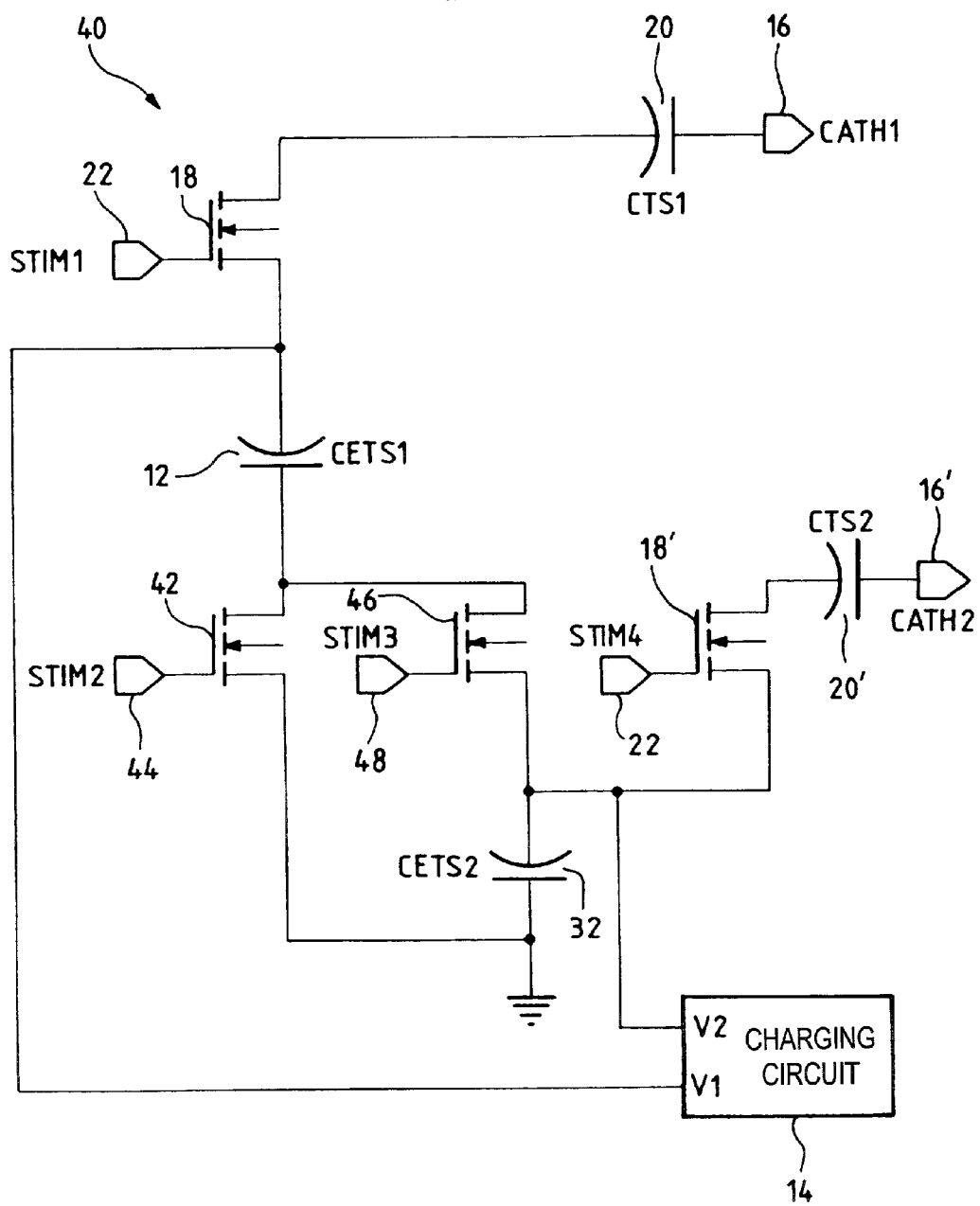

STIMULATION CIRCUITS FOR A CYCLE TO CYCLE STIMULATION THRESHOLD CAPTURE FOR AN ACTIVE IMPLANTABLE CARDIAC DEVICE

FIELD OF THE INVENTION

The present invention is directed to "active implantable medical devices" as such devices are defined by the Jun. 20, 1990 directive 90/385/CEE of the Council of the European Communities, more precisely to pacemaker, defibrillator and/or cardiovertor devices that are able to deliver to the heart pulses of low energy for the treatment of the disorders of the heart rate. It more particularly relates to the adjustment of the amplitude (voltage level) of the stimulation pulses over the course of time.

BACKGROUND OF THE INVENTION

The voltage level required to cause a stimulation of the cardiac cavities (ventricular or atrial) is a value typically ranging between 1.5 and 7.5 V, adjustable in step increments of 0.5 V. The amplitude must of course be sufficiently high to cause the depolarization of the myocardium; it is, however, also necessary to avoid too high a value to maximize the lifespan of the power source, because the stimulation energy applied to the myocardium, and thus the corresponding energy consumption of the device, is proportional to the square of the amplitude (and also to the duration) of the pulse delivered.

The test of the effectiveness of the stimulation, i.e., whether the amplitude is sufficient to cause a depolarization, also called a "capture test", can be carried out at regular intervals, for example every six hours. An automatic test algorithm can be used, such as the algorithm described in the international patent publication WO-A-93/02741, and its counterpart U.S. Pat. No. 5,411,533, commonly assigned to the assignee hereof, Ela Medical. The U.S. Pat. No. 5,411,533 is incorporated herein by reference for the entirety of its disclosure, and in particular the capture test disclosed therein. The capture test essentially identifies a capture threshold amplitude above which a stimulation is effective and below which a stimulation pulse is ineffective. The capture test also may be performed when there is a lost of capture (also known as having a "lost capture"), a condition that occurs when the voltage amplitude required to cause a myocardial contraction either increases spontaneously, or the stimulation voltage applied is decreased by device control, as may occur from time to time. The stimulation pulse amplitude is then adjusted on the basis of the capture threshold thus determined plus a large safety margin. To account for the safety margin, the adjusted level is typically set as twice the measured capture threshold value, between a minimum (typically 1.5 V) and a maximum (typically 5.0 V) limit.

Another technique to which the present invention is referred concerns operating a capture test "cycle to cycle", i.e., to examine each cardiac cycle to determine whether an applied stimulation was effective. For this purpose, the stimulation voltage is maintained near to the determined threshold voltage at which capture is lost. In the event of a rise in the capture threshold for the patient, the loss of capture (i.e., an ineffective stimulation) is detected by examining cardiac activity during an interval (also called a window), which follows delivered stimulation pulse, typically during the following 63 ms, and determining that there was no myocardial contraction during the window and the stimulation was ineffective. This detection of loss of capture has two consequences. First, at the next stimulation, the stimulation voltage level will be adjusted, i.e., increased by one step, to compensate for the rise in the capture threshold of the patient. Second, and importantly, a backup-stimulation pulse having a higher energy level must be applied immediately (i.e., at the end of the 63 ms window following an ineffective stimulation) to compensate for the absence of a depolarization (spontaneous or stimulated) of the myocardium.

This cycle to cycle technique is particularly advantageous because it permits one to be freed from using the large incremental safety margin in stimulation voltage amplitude applied when the capture threshold was measured only at periodic intervals, for example, every six hours. The lifespan of the power supply based on reduced energy consumption during stimulation can thus be lengthened in a substantial manner. However, the much more frequent need for delivering a backup-stimulation pulse can disturb the operation of pacemaker and can induce an energy consumption that is likely to reduce in the end the benefits from reducing energy consumption obtained by the use of the "cycle to cycle" capture technique. It also is essential in this technique not to delay the backup-stimulation, because such a delay would create a physiological risk for the patient.

OBJECTS AND SUMMARY OF THE INVENTION

It is, therefore, an object of the present invention is to propose a new configuration for the stimulation circuits that is able to avoid the foregoing risks at the time of the use of a technique where the capture is tested cycle to cycle, i.e., where the stimulation voltage is maintained near to the voltage at which there is a loss of capture. Broadly, the present invention concerns an active implantable medical device of the above-mentioned generic type, i.e., comprising at least one stage for the stimulation of a cardiac cavity having an output capacitor; a circuit for charging the output capacitor to a predetermined stimulation voltage near to the capture threshold of effectiveness of stimulation of the patient carrying the device; a first switch that is able to connect the output capacitor to a stimulation output terminal of the device, the terminal being connectable to a stimulation electrode; means for performing a capture test that is able to determine, after delivery of a stimulation pulse, if the stimulation pulse was effective or if there was a loss of capture; means for readjusting the stimulation voltage according to the result of the capture test; and means for delivering a backup-stimulation after the capture test if the result of capture test reveals a loss of capture.

According to the invention, the means for delivering a backup-stimulation pulse includes an additional capacitor and a second switch able to connect the additional capacitor to the aforementioned stimulation terminal of the device.

In a first embodiment, the additional capacitor is a second capacitor, distinct from the output capacitor of the aforementioned stimulation stage, and the charging circuit also is able to charge this second capacitor to a backup-stimulation voltage that is higher than the aforementioned stimulation voltage. The charging circuit may be configured to have two programmable voltage outputs, or one such output such that the programmable charging voltage can be easily selected.

In a second embodiment, the additional capacitor includes an additional capacitor such that the charging circuit also is able to charge separately the additional capacitor to a voltage level, and the second switch is able to connect the additional capacitor in series with the output capacitor during the delivery of a backup-stimulation pulse.

In either embodiment, if it is envisaged to have at least two distinct stages of stimulation, e.g., a dual chamber device, the aforementioned second capacitor or additional capacitor can be advantageously an output capacitor belonging to a second stimulation stage (other than the aforementioned stimulation staged, for example, one of the respective stimulation stages for right atrial/ventricular, left atrial/ventricular, right ventricular/left ventricular (or conversely) cardiac cavities.

The second embodiment can be realized in particular by a configuration in which: the output capacitor has a first plate that is connected both to a first output of the capacitor charging circuit and to a first switch selectively connected to a first stimulation terminal, the output capacitor has a second plate connected to a second switch selectively connected to a ground potential, an additional capacitor that has a first plate connected to a second output of the capacitor charging circuit and to a third switch selectively connected to a second stimulation terminal, and a fourth switch selectively connected to the output capacitor second plate and the additional capacitor first plate.

BRIEF DESCRIPTION OF THE DRAWINGS

Other features, characteristics and advantages of the present invention will appear to a person of ordinary skill in the art in view of the following detailed description, made with reference to the drawings annexed, in which like reference characters refer to like elements, and in which:

FIG. 1 is a schematic drawing of a first embodiment of the present invention; and FIG. 2 is a schematic drawing of a second embodiment of the present invention.

DETAILED DESCRIPTION OF THE INVENTION

With reference to FIG. 1, reference 10 indicates generally the output stage of a pacemaker generator. The stimulation pulse is obtained by the discharge of a capacitor 12, the CETS1 capacitor, previously charged to a charging voltage V1 by a charging circuit 14. Charging circuit 14 is typically a voltage multiplier that can generate a steady voltage that is a multiple of the power supply voltage (not represented) of the pacemaker. Such charging circuits are known in the art and any suitable charging circuit may be used.

The voltage is regulated in order to stop charging when the desired programmed voltage level V1 stored on capacitor 12 is reached. The voltage V1 generally lies between 1.0 and 7.5 V, and is preferably adjustable in step increments of 0.5 V. The value of capacitor 12 is generally 10 $\mu F$.

The charge stored in capacitor 12 is transferred towards an output (CATH) 16 within the pacemaker, which output is, for example, connected to the distal electrode of an atrial or ventricular stimulation probe (not shown). The discharge is controlled by turning on and off transistor 18 having a grid (base) controlled by a signal STIM applied to terminal 22. The discharge is delivered via a coupling capacitor CTS, reference 20, also typically 10 $\mu F$. CTS capacitor 20, in addition to its function of blocking the creation of a D.C. current, operates to protect the patient against a possible D.C. current in the event of failure of the stimulation transistors, e.g., transistor 18.

After stimulation, CTS capacitor 20 (which is charged during the stimulation) is discharged by a ground connection when transistor 24 is made conducting. The grid (base) is controlled by an OCD (Output Capacitor Discharge) signal applied to terminal 26. Resistor 28, typically 20 K$\Omega$, allows the complete discharge of CTS capacitor 20 after the opening of transistor 24, and also ensures a compensation of the leakage currents in the circuit.

According to this illustrated configuration of a stimulation stage, if one functioned in a "cycle to cycle capture" mode, i.e., with a stimulation voltage close to the threshold voltage at which there is a loss of capture, to start a backup-stimulation with a greater amount of energy than the ineffective stimulation pulse it would be necessary to recharge capacitor 12 during a window following stimulation when the capture test is conducted. This window is typically 63 ms. To deliver an effective back-up stimulation pulse, the recharge must be great enough to cause stimulation and must occur during every cardiac cycle for safety reasons. In other words, it is not desirable to delay a backup-stimulation pulse to allow for recharging capacitor 12 after detection of an ineffective stimulation, because this would disturb the operation of the pacemaker. Rather, the recharge must be complete by the end of the window so a back-up stimulation pulse can be delivered promptly.

The invention proposes to supplement this configuration, in itself known, by the circuit included within the framework in dotted lines 30, in order to be able, in the event of loss of capture, to immediately apply a backup-stimulation having a greater energy level and without an unacceptable over-consumption of power or, stated otherwise, with improved energy conservation. More precisely, the invention proposes to add a capacitor CETS2, reference 32, "permanently" charged with a voltage V2 that is higher than voltage V1 of capacitor 12. This charging voltage V2 is advantageously delivered by the same charging circuit 14 used to produce the voltage V1 on capacitor 12.

In this embodiment, CETS2 capacitor 32 is used only to deliver the backup-stimulation. Thus, for as long as the capture is effective, capacitor 32 is simply maintained with its nominal charging voltage V2, involving in this case only a leakage current to maintain the charge, and hence contemplating a negligible incremental consumption of energy. On the other hand, in the event of loss of capture, charged capacitor 32 is discharged towards stimulation terminal 16 to ensure prompt delivery of the backup-stimulation pulse, by closing transistor 34 under the control of a STIM2 signal applied at 36. Capacitor 32, being always charged, is therefore immediately able to perform its role, so that backup-stimulation could be applied without delay at the end of the detection interval (window) in the absence of capture.

Like capacitor 12, backup-stimulation capacitor 32 is discharged through terminal 16 via the coupling capacitor 20, that will in turn be discharged by the transistor 24 and resistor 28 after backup-stimulation, in the same manner as capacitor 12 is discharged following a normal stimulation.

In the first embodiment just described (with reference to FIG. 1), the backup-stimulation capacitor 32 is a dedicated capacitor, specific to this function.

With an aim in particular of the reduction of costs, the role of the dedicated additional capacitor can be played by an existing capacitor within the pacemaker, as soon as the terminal voltage is higher than that of the stimulation capacitor 12. This existing capacitor can be in particular the output capacitor for another stage of stimulation, such as the stage for the left ventricular stimulation, the atrial stimulation or any other available stage of stimulation, particularly in multisite devices, provided that this other existing capacitor is not to be used simultaneously for both the back-up stimulation and its regular stimulation.

FIG. 2 thus illustrates a second embodiment, according to this principle. The two stages of stimulation 40 comprises two stimulation capacitors CETS1 and CETS2, respectively references 12 and 32, charged in a manner discussed below by a charging circuit 14 that is able to generate corresponding voltages V1 and V2. The discharge can be operated on two output terminals CATH1 and CATH2, referred respectively 16 and 16'. The discharge on terminal 16 is operated by closing transistors 18 and 42 (to bring to ground potential the opposite plate of capacitor 12), controlled by application of control signals STIM1 and STIM2 on corresponding terminals 22 and 44. The discharge on terminal 16' is similarly operated by closing of transistor 18', controlled by application of a control signal STIM4 on corresponding terminal 22'.

The discharge currents are applied at terminals 16 and 16' via CTS1 and CTS2 connection capacitors 20 and 20' (by simplification, the transistors and resistances that are employed to manage the discharge of the connection capacitors 20 and 20' after stimulation or backup-stimulation are not represented, and it should be understood that these components are identical to the components 24, 26 and 28 illustrated in FIG. 1).

Terminal 16 being connected to the right ventricle electrode stimulation terminal 16' is, for example, connected to the left ventricle stimulation electrode, or the stimulation electrode of an atrium.

Transistors 42 and 46, controlled by signals STIM2 and STIM3 applied to respective terminals 44 and 48, make it possible to connect together capacitors 12 and 32 so as to use them either separately, or in series to add the voltages on their outputs. Transistor 42 is connected between one of the plates of capacitor 12 (opposite to the plate connected to discharge transistor 18) and the ground. Transistor 46 is connected between this same plate of capacitor 12 and the plate of capacitor 32 connected to the discharge transistor 18', the other capacitor 32 plate being connected directly to the ground potential.

Transistors 18, 18', 42 and 46 are controlled in the following way, according to whether one wishes to charge one or the other of the capacitors, or to discharge one or the other of the capacitors, or to apply a backup-stimulation. In the explanation which follows, one supposes, when that is not specified, that the transistors all be in a blocking state (i.e. in open circuit):

1) charging capacitor 12 by circuit 14 to the voltage V1: closing (conduction step) transistor 42;

2) charging capacitor 32 by the circuit 14 to the voltage V2: all the transistors (in particular transistor 46) remain open;

3) stimulation at voltage V1 on terminal 16: closing of transistors 18 and 42 (transistor 46 remaining open) so as to allow the discharge of capacitor 12 charged to voltage V1;

4) application of a backup-stimulation on loss of capture: closing of transistors 18 and 46 (transistor 42 remaining open), which places capacitors 12 and 32 in series and thus to apply on terminal 16 the cumulative voltages of V1 and V2, thanks to the additional energy contributed by the voltage V2 on capacitor 32;

5) stimulation of voltage V2 on terminal 16': closing of transistor 18' (transistor 46 remaining open) so as to allow the discharge of capacitor 32 charged to the voltage V2 level.

It should be understood that control of the switches, i.e., the transistors, is preferably maintained under software control in a microprocessor controlled active implantable medical device, such that the various control signals are binary commands that operate the turn the selected transistors between off and on states as and when appropriate. Similarly, the adjustment of the stimulation voltage can be obtained under microprocessor control by increasing stepwise the stimulation voltage amplitude when capture is lost, and making a corresponding adjustment in the charging circuit to produce the corresponding charging voltage. Suitable software instructions to produce the desired control signals for the circuit structures disclosed herein in a microprocessor controlled device are deemed to be well within the ability of a person of ordinary skill in the art.

One skilled in the art will appreciate that the present invention can be practiced by other than the described embodiment, which are presented for the purposes of illustration and not of limitation. Indeed, the circuit parameters and values for voltages and components should be considered merely as illustrative of useful values, but should not be viewed as limiting as these values may be changed without departing from the present invention.

We claim:

1. An active implantable medical device comprising:
a first and a second stimulation stage of a cardiac cavity,
said first stimulation stage comprising:
an output capacitor,
a stimulation terminal,
a charging circuit to charge a capacitor to a predetermined stimulation voltage that is near to an effective threshold for stimulation of the patient carrying the device,
a first switch able to connect the output capacitor to the stimulation terminal,
means for performing a capture test able to determine whether a delivered stimulation is effective or there was loss of capture,
means for adjusting the stimulation voltage according to whether a delivered stimulation is effective, and
means for delivering a backup-stimulation after the capture test determined a loss of capture,
said device being further characterized in that the means for delivering a backup-stimulation comprises;
an additional capacitor capable of storing a second predetermined voltage,
a second switch to connect said additional capacitor to discharge said second predetermined voltage to said stimulation terminal,
said additional capacitor further comprising a specific capacitor, distinct from said output capacitor, wherein the charging circuit is able to charge said specific capacitor to said second predetermined voltage, wherein said second predetermined voltage is higher than said first predetermined stimulation voltage,
said second stimulation stage comprising a second output capacitor and a second stimulation terminal, wherein said specific capacitor further comprises said second output capacitor of said second stimulation stage, and wherein said first switch connects said specific capacitor in series with said output capacitor.

2. An active implantable medical device comprising:
a first and a second stimulation stage of a cardiac cavity,
said first stimulation stage comprising:
an output capacitor,
a stimulation terminal, a charging circuit to charge a capacitor to a predetermined stimulation voltage that is near to an effective threshold for stimulation of the patient carrying the device, a first switch able to connect the output capacitor to the stimulation terminal, means for performing a capture test able to determine whether a delivered stimulation is effective or there was loss of capture, means for adjusting the stimulation voltage according to whether a delivered stimulation is effective, and means for delivering a backup-stimulation after the capture test determined a loss of capture, said device being further characterized in that the means for delivering a backup-stimulation comprises;

an additional capacitor capable of storing a second predetermined voltage, a second switch to connect said additional capacitor to discharge said second predetermined voltage to said stimulation terminal, said additional capacitor further comprising a specific capacitor, distinct from said output capacitor, wherein the charging circuit is able to charge said specific capacitor to said second predetermined voltage, wherein said second predetermined voltage is higher than said first predetermined stimulation voltage, said second stimulation stage comprising a second output capacitor and a second stimulation terminal, wherein said specific capacitor further comprises said second output capacitor of said second stimulation stage, and wherein said additional capacitor further comprises an additional capacitor and wherein said charging circuit is coupled to charge said additional capacitor to the second predetermined voltage separately from said output capacitor, and the second switch further comprises means for connecting in series the output capacitor and the additional capacitor during a delivery of backup-stimulation.

3. The device of claim 2, wherein the charging circuit has a first output and a second output, the device further comprises a ground potential, the output capacitor has a first plate connected to the first output of the charging circuit and to said first switch connected selectively to the stimulation terminal, the output capacitor has a second plate connected to a third switch connected selectively to the ground potential, the additional capacitor has a first plate connected to the second output of the charging circuit and to a fourth switch connected selectively to a second stimulation terminal, and a fifth switch selectively connected to the output capacitor second plate and the additional capacitor first plate.

4. The device of claim 2, further comprising a second stimulation stage distinct from said first stimulation stage, said second stimulation stage comprising a second output capacitor and a second stimulation terminal, and wherein said additional capacitor comprises said second output capacitor of said second stimulation stage.

5. The device of claim 4, wherein said first stimulation stage is one of an atrial stage and a right ventricular stage, and said second stimulation stage is the other of the atrial stage and the right ventricular stage.

6. The device of claim 4, wherein said first stimulation stage is one of an atrial stage and a left ventricular stage, and the second stimulation stage is the other of the atrial stage and the left ventricular stage.

7. The device of claim 4, wherein said first stimulation stage is one of a right ventricular stage and a left ventricular stage and the second stimulation stage is the other of the right ventricular stage and the left ventricular stage.

8. An active implantable medical device comprising:

at least a first stimulation stage of a cardiac cavity, said first stimulation stage comprising:

an output capacitor;

a stimulation terminal;

a charging circuit to charge a capacitor to a predetermined stimulation voltage that is near to an effective threshold for stimulation of the patient carrying the device;

a first switch able to connect the output capacitor to the stimulation terminal;

means for performing a capture test able to determine whether a delivered stimulation is effective or there was loss of capture;

means for adjusting the stimulation voltage according to whether a delivered stimulation is effective; and means for delivering a backup-stimulation after the capture test determined a loss of capture, said device being further characterized in that the means for delivering a backup-stimulation comprises;

a first additional capacitor capable of storing a second predetermined voltage and a second switch to connect said additional capacitor to discharge said second predetermined voltage to said stimulation terminal, wherein said first additional capacitor further comprises a second additional capacitor and wherein said charging circuit is coupled to charge said first additional capacitor to the second predetermined voltage separately from said output capacitor, and the second switch further comprises means for connecting in series the output capacitor and said first additional capacitor during a delivery of backup-stimulation;

wherein the charging circuit has a first output and a second output, the device further comprises a ground potential, the output capacitor has a first plate connected to the first output of the charging circuit and to said first switch connected selectively to the stimulation terminal, the output capacitor has a second plate connected to a third switch connected selectively to the ground potential, the additional capacitor has a first plate connected to the second output of the charging circuit and to a fourth switch connected selectively to a second stimulation terminal, and a fifth switch selectively connected to the output capacitor second plate and the additional capacitor first plate.

9. An active implantable medical device comprising:

at least a first stimulation stage of a cardiac cavity, said first stimulation stage comprising:

an output capacitor;

a stimulation terminal;

a charging circuit to charge a capacitor to a predetermined stimulation voltage that is near to an effective threshold for stimulation of the patient carrying the device;

a first switch able to connect the output capacitor to the stimulation terminal;

means for performing a capture test able to determine whether a delivered stimulation is effective or there was loss of capture;

means for adjusting the stimulation voltage according to whether a delivered stimulation is effective; and means for delivering a backup-stimulation after the capture test determined a loss of capture, said device being further characterized in that the means for delivering a backup-stimulation comprises;

a first additional capacitor capable of storing a second predetermined voltage and a second switch to connect said additional capacitor to discharge said second predetermined voltage to said stimulation terminal, wherein said first additional capacitor further comprises a second additional capacitor and wherein said charging circuit is coupled to charge said first additional capacitor to the second predetermined voltage separately from said output capacitor, and the second switch further comprises means for connecting in series the output capacitor and said first additional capacitor during a delivery of backup-stimulation;

a second stimulation stage distinct from said first stimulation stage, said second stimulation stage comprising a second output capacitor and a second stimulation terminal, and wherein said first additional capacitor comprises said second output capacitor of said second stimulation stage.

10. The device of claim 9, wherein said first stimulation stage is one of an atrial stage and a right ventricular stage, and said second stimulation stage is the other of the atrial stage and the right ventricular stage.

11. The device of claim 9, wherein said first stimulation stage is one of an atrial stage and a left ventricular stage, and the second stimulation stage is the other of the atrial stage and the left ventricular stage.

12. The device of claim 9, wherein said first stimulation stage is one of a right ventricular stage and a left ventricular stage and the second stimulation stage is the other of the right ventricular stage and the left ventricular stage.

* * * * *